United States Patent [19]

Rossi et al.

[11] Patent Number: 4,578,511

[45] Date of Patent: Mar. 25, 1986

[54] METHOD OF PREPARING PURE BENZOIC ACID

[75] Inventors: Pietro P. Rossi, Garlasco; Paolo Senni, Colleferro; Sergio Ferruzzi, Trieste, all of Italy

[73] Assignees: Chimica del Friuli S.p.A., Torviscosa; Snia BPD S.p.A., Milan, both of Italy

[21] Appl. No.: 587,896

[22] Filed: Mar. 9, 1984

[30] Foreign Application Priority Data

Mar. 11, 1983 [IT] Italy ............................... 20042 A/83

[51] Int. Cl.$^4$ ............................................. C07C 51/42
[52] U.S. Cl. .................... 562/494; 562/493; 562/412; 562/413; 562/414
[58] Field of Search ................ 562/494, 412, 413, 414

[56] References Cited

U.S. PATENT DOCUMENTS 3,235,588  2/1966  Weaver ............................... 562/494
3,660,478  5/1972  Nasser ................................. 562/494
3,931,305  1/1976  Fisher ................................. 562/494

Primary Examiner—Paul J. Killos
Attorney, Agent, or Firm—Wenderoth, Lind & Ponack

[57] ABSTRACT

The invention is concerned with a method of purifying benzoic acid, as obtained by catalytic oxidation of toluene and purification by rectification with the secondary streams being cycled back into the oxidation reactor, characterized in that the secondary streams flowing out of the stripping column undergo the following sequential steps: (a) at least one distillation and at least one crystallization in an organic solvent; (b) scrubbing of the crystals obtained from (a) with the same solvent as in (a); (c) cycling of the mother liquors from crystallization in (a) plus the scrubbing liquors as in (b) back into the dissolver; (d) further scrubbing of the crystals from (b) with the same solvent as in (a) and cycling back of the scrubbing liquors, the crystals scrubbed as in (d) being optionally (d1) further scrubbed with water.

2 Claims, 2 Drawing Figures

METHOD OF PREPARING PURE BENZOIC ACID

BACKGROUND OF THE INVENTION

1. Field of the Invention

This invention relates to a method of preparing high purity benzoic acid at a high yield from crude benzoic acids obtained by individual oxidation of toluene. The invention is also concerned with the benzoic acid prepared thereby.

In catalytically oxidizing toluene with air to produce benzoic acid, byproducts of various nature are coproduced, such as benzaldehyde, benzyl alcohol, diphenyl, 2- and 3-methyldiphenyl, benzylbenzoate, diphenylcarboxylic acids, etc. Such byproducts accompany the toluene and benzoic acid leaving the oxidation reactor and must be separated if a suitable benzoic acid for industrial and pharmaceutical applications is to be obtained.

2. Prior Art

Toluene oxidation to prepare benzoic acid, and purification of the latter, is disclosed for example in UK Pat. No. 1,219,453 and French Pat. No. 1,560,868. In essence, such prior processes are based on oxidation of toluene with pressurized air at 6-15 atmospheres and 150° to 180° C., and in the presence of suitable catalysts, such as Co-Mn, on distillation first of the non-converted toluene which accompanies the benzoic aicd, followed by purification by rectification of the benzoic acid in a tray column, wherein benzaldehyde, benzyl alcohol, toluene left-overs, and other byproducts still present in minor amounts separate as overheads; this stream, which contains appreciable amounts of benzoic acid, is usually cycled back to the oxidation reactor.

With other conventional methods, benzaldehyde is separated from the stream, as by stripping and rectifying arrangements, while the volatile fraction and residue from this separation are returned to the oxidation reactor. The end products from primary rectification of benzoic acid are further distilled with a secondary rectification to obtain benzoic acid, albeit at a strength not exceeding 80%, which is passed to the oxidation reactor. The residue from this second distillation, which contains the high-boiling impurities, is burned off. From the primary rectification column benzoic acid is yielded at a strength of approximately 99%. Impurities may have on the average the following composition: diphenyl, 2- and 3-methyldiphenyl, etc.

When operating in accordance with the above prior art, such cycling of the overhead products from primary rectification (or of overhead and end products after benzaldehyde has been recovered) and secondary rectification distillate back to the reactor has two main disadvantages, namely:

(1) The content in byproducts of the streams flowing from the oxidation reactor to the primary rectification column is increased, until such byproducts find their outlet either through the end products from the second rectification, or secondary rectification, or production; this affects the quality of the resulting benzoic acid;

(2) Decreased capacity of the oxidation reactor; in fact, the rate of oxidation of toluene with a soluble catalyst and air is inversely proportional to the concentration of benzoic acid in the oxidation reactor toluene; for example, with benzoic acid concentrations in excess of 35%, and operating at temperatures in the 155° to 180° C. range and pressures in the order of 6-15 atmospheres, reaction stops. Thus, cycling large amounts of benzoic acid back to the oxidation reactor results in a decreased output.

SUMMARY OF THE INVENTION

The Applicants have now unexpectedly found that it is possible to increase the reactor productivities, and at the same time achieve high purity benzoic acid at a high yield, if the overhead product from the primary rectification column and distillate from the secondary rectification column, and/or the crude products from benzaldehyde separation which contain a relatively large overall amount of byproducts, are purified with a crystallization system on a continuous basis from a suitable organic solvent, such as toluene, which provides for intense recycling of mother liquors and limited expurgation thereof, such that the amount of benzoic acid wasted to the expurgation of mother liquors can be greatly reduced.

In fact, while it is not surprising that pure benzoic acid can be obtained from crude benzoic acid by crystallization, it is indeed surprising that pure benzoic acid can be obtained by using for crystallization mother liquors which may be quite rich in byproducts.

For comparison, shown here below are purity patterns of benzoic acid product versus the byproducts/benzoic acid ratio in the solution to be crystallized (solvent being toluene):

| Concentration of benzoic acid in the solution to be crystallized | Impurities/benzoic acid ratio (by weight) | Gas-chromatographic purity of the benzoic acid resulting from crystallization |
| --- | --- | --- |
| 33.0% | .1 | .1% |
| 36.7% | .25 | .16% |
| 22.4% | .5 | .24% |
| 25.0% | .7 | .22% |
| 24.6% | .73 | .21% |
| 29.5% | .9 | .14% |
| 36.7% | 1.0 | .15% |

Thus, it is an object of this invention to provide a method of purifying benzoic acid, as obtained by catalytic oxidation of toluene and purification by rectification wherein the secondary streams are cycled back into the oxidation reactor, characterized in that the secondary streams leaving the stripping column are caused to undergo the following sequential steps:

(a) at least one distillation and at least one crystallization in an organic solvent;

(b) scrubbing of the crystals from (a) using the same solvent as in (a);

(c) cycling of the mother liquors from the crystallization as in (a) plus the mother liquors from (b) back into the dissolver;

(d) further scrubbing of the crystals from (b) using the same solvent as in (a), the scrubbing liquors being cycled back; and optionally (d1) further scrubbing of the crystals as scrubbed in (d) with water.

Where as the solvent for (a), (b) and (c) above toluene is used, the scrubbing liquors are cycled back to the toluene oxidation reactor.

The increased capacity to be obtained for the oxidation reactors when operating in accordance with the method of this invention will be illustrated next in comparison with the output of prior methods.

Assuming that a maximum concentration of 30% benzoic acid can be obtained commercially, as contained in the oxidation reactors in the stationary phase and in continuous processes, the following results have been noted: (A) by operating in conformity with prior methods, that concentration is formed by the quota of benzoic acid yielded by the reaction plus the quota of benzoic acid cycled back to the reactors along with the secondary streams from the primary and secondary rectification columns (which generally accounts for 5% of the 30% concentration of benzoic acid); in other words, to produce 100 parts final benzoic acid, according to prior methods, 120 parts are to be passed into the reactor, of which parts 20 are recyclate; (B) by operating in conformity with the method of the instant invention, the oxidation system can yield effectively 120 parts benzoic acid (as against the 100 parts to be obtained conventionally).

An added advantage afforded by operation in accordance with the method of this invention resides in the improved quality of the benzoic acid yielded by the primary rectification column; in fact, by avoiding cycling of the benzoic acid and byproducts back to the oxidation reactor, the benzoic acid flowing to the first rectification column is purer. From rectification, a benzoic acid is obtained which has an improved strength of 99.2%, as against 99% to be attained when operating in accordance with the prior art teachings.

A preferred but not limitative "flow sheet" of how the inventive method may be implemented (as shown in FIGS. 1 and 2 of the accompanying drawings, where letter symbols refer to the reaction apparata, the numerals in brackets indicating the process streams) will now be described.

Toluene (2) and air (1), with cobalt benzoate for a catalyst, are passed continuously into an oxidation reactor R1. The reactor is maintained in the 160° to 180° C. temperature range at a pressure of 8-15 atmospheres; nitrogen and toluene issue from the reactor at (3).

The reaction product (4) containing non-converted toluene, 25% to 35% benzoic acid, about 2% benzaldehyde, and other derivatives and byproducts, is passed to S4 where it is depressurized to ambient pressure. A part of the toluene (5) is distilled during this step.

The remaining solution (6) is sent to a still C1 where another quota of toluene (7) is distilled. The remainder of the solution, which contains benzoic acid, benzaldehyde, benzyl alcohol, byproducts, and still a part of toluene (8), is passed into the primary stripping column C2.

An overhead stream (10) issues from the column which contains toluene, benzoic acid, benzaldehyde, benzyl alcohol, etc., these being delivered to benzaldehyde recovery. A stream (11) is returned from this recovery which contains benzoic acid and byproducts.

From the first tray in the primary rectification column there issue toluene, benzoic acid, and byproducts (9). Production benzoic acid issues from (13). The distillation end products C2 are delivered to the secondary stripping column C3 whence crude benzoic acid flows out of (14), while heavy byproducts with minor amounts of benzoic acid issue from (15).

With prior methods, the streams (9), (11) and (14) would be returned to the oxidation reactor, whereas with the method of this invention they are delivered to purification by crystallization.

This is accomplished in conformity with the block diagram of FIG. 2.

The combined streams (9), (11) and (14) are introduced at (1) into a dissolver D1, while at (13) are introduced the mother liquors of crystallization in a toluene solution. The temperature of the dissolver D1 is maintained at 50°-110° C. under a pressure not exceeding atmospheric pressure.

Within the dissolver, an inert gas atmosphere is maintained. The benzoic acid and byproducts dissolved in toluene which issue from D1 are conveyed as a stream (2) into a crystallizer CR wherein a temperature of 10°-40° C. is maintained at a pressure equal to or lower than atmospheric pressure.

The concentration of benzoic acid in CR is of 20-40%, the concentration of the by-products is of 20-40%.

From CR, the crystal suspension in mother liquors is passed as a stream (3) into a centrifuge CE (or any suitable appartus for separating the crystals out of the liquid), wherein the crystals are separated and the mother liquor (12) caused to flow back into the dissolver D1. From (11), expurgation of the mother liquors is effected in such amounts as to virtually remove all of the byproducts introduced at (1).

The crystals flowing out of CE as a stream (4) are delivered into a centrifuge CE1 (or any suitable device to separate the crystals from the liquid) wherein they are scrubbed with toluene; it being possible to optionally scrub the crystals in the centrifuge CE itself. The scrubbing liquors (10) flowing out of CEL1 are passed into the dissolver D1.

The crystals issuing from CEL1 as a stream (5) are again scrubbed in CEL2 with toluene (8), whereas the scrubbing liquors (7), essentially comprisng toluene, are delivered to the oxidation reactor. The benzoic acid crystals issue from (6) and are stripped of toluene leftover with conventional methods (e.g., by vacuum drying or steam stripping). If desired, the crystals may be stripped of toluene by scrubbing in water.

The pure benzoic acid obtained through the inventive method just described is also an object of this invention.

DETAILED DESCRIPTION OF THE PREFERRED EMBODIMENTS

The following Example is illustrative of this invention, but constitutes no limitation to the invention true scope.

Benzoic acid is designated "AB" in the Example for simplicity.

EXAMPLE

OXIDATION OF TOLUENE

A. OXIDATION AND PURIFICATION OF TOLUENE

Figure 1:
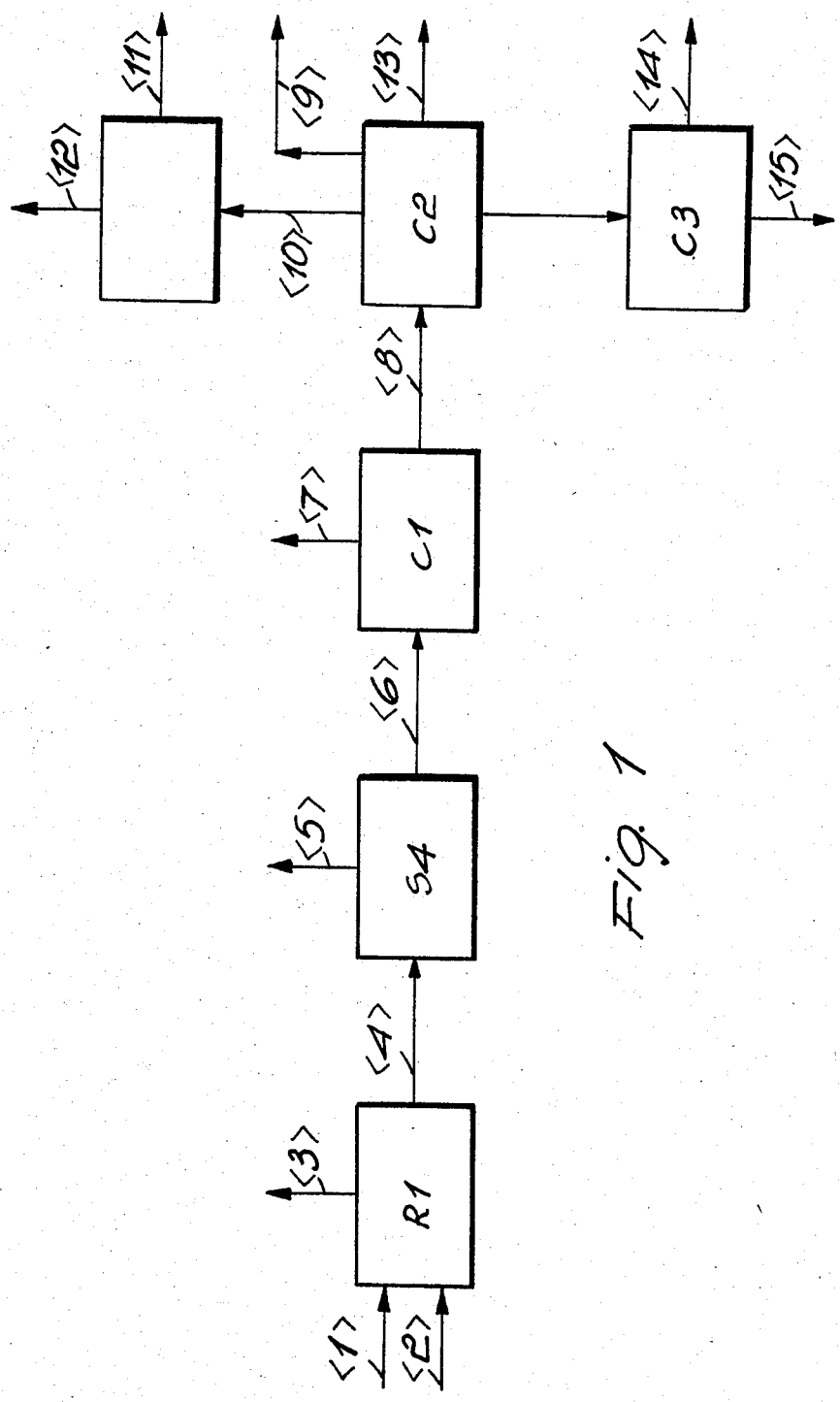

In accordance with the oxidation scheme shown in FIG. 1 of the drawings, shown are the main process streams per 100 parts by wieght of benzoic acid being produced hourly on a continuous basis.

| In accordance with the oxidation scheme shown in FIG. 1 of the drawings, shown are the main process streams per 100 parts by weight of benzoic acid being produced hourly on a continuous basis. | | | | | | |
|---|---|---|---|---|---|---|
| Streams | (4) | (9) | (11) | (13) | (14) | (15) |
| Toluene | 410 | 1.87 | — | — | — | — |
| Benz- | 11.7 | 0.26 | 2.0 | — | — | — |

-continued

In accordance with the oxidation scheme shown in FIG. 1 of the drawings, shown are the main process streams per 100 parts by weight of benzoic acid being produced hourly on a continuous basis.

| Streams | (4) | (9) | (11) | (13) | (14) | (15) |
|---|---|---|---|---|---|---|
| aldehyde | | | | | | |
| Benzoic acid | 134 | 12.4 | 7.7 | 100 | 2.49 | 1.9 |
| Benzyl alcohol | 1.8 | 0.3 | 1.5 | — | — | — |
| By-products | 15.5 | 2.15 | 7.9 | 1.3 | 0.68 | 3.4 |
| TOTAL | 573 | 16.98 | 19.2 | 101.3 | 3.2 | 5.3 | which, following drying off toluene, shows a gas-chromatographic purity of 99.8%.

Thus, the plant hourly output of benzoic acid is 100+20.83=120.83 parts by weight, as against 100 parts by weight/hour of prior methods. The composition of the solution of AB, toluene, and byproducts whence crystallized benzoic acid is obtained, is shown as a stream (2) in the following Table, which also shows the compositions of the main streams in the purification process by crystallization. In this stream (2), the ratio of byproducts to benzoic acid is 0.948, that is, practically one part benzoic acid is accompanied by one part byproducts. For convenience of illustration, each stream has been subdivided into its three basic species, namely toluene, benzoic acid, and byproducts.

Figure 2:
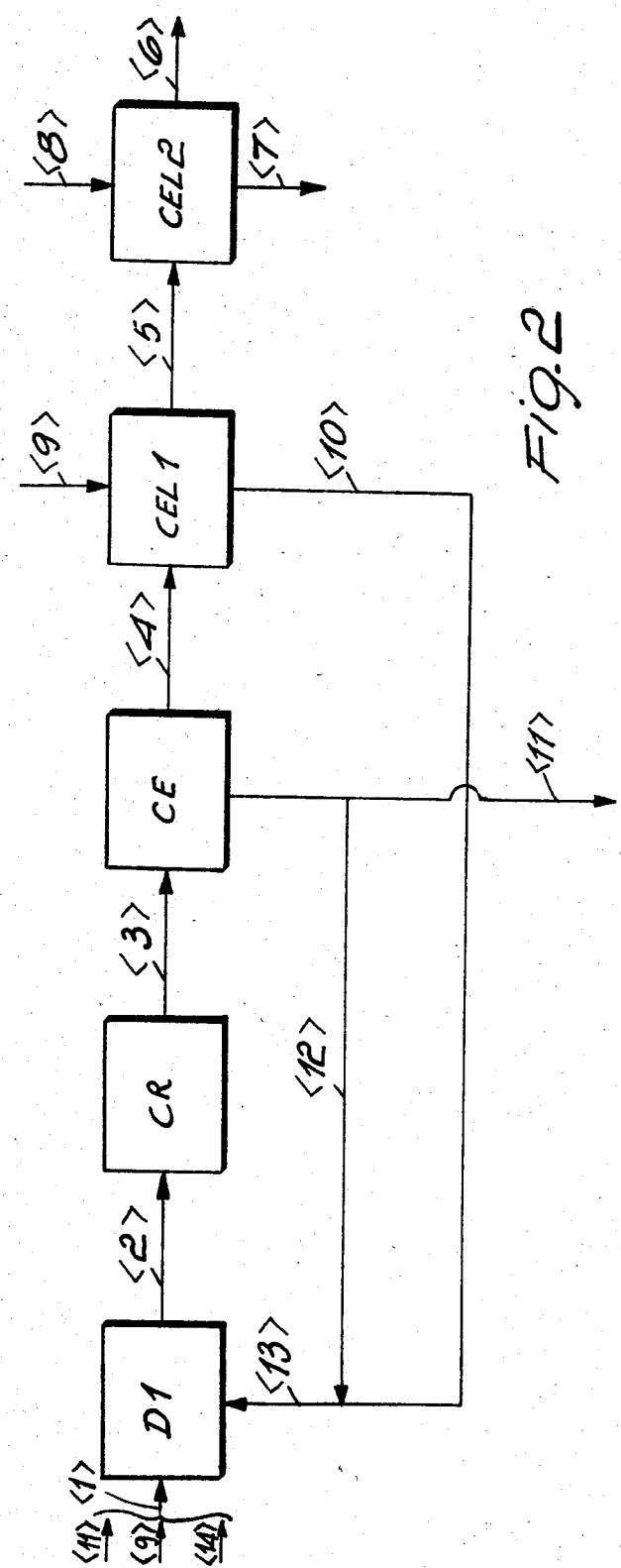

| | CRYSTALLIZATION OF BENZOIC ACID AS OBTAINED IN ACCORDANCE WITH THE "FLOW SHEET" DIAGRAM OF FIG. 2 | | | | | | | | | |
|---|---|---|---|---|---|---|---|---|---|---|
| Streams | (1) | (2) | (4) | (5) | (6) | (7) | (10) | (11) | (12) | (13) |
| Toluene | 1.86 | 30.37 | 2.68 | 2.95 | 2.84 | 6.98 | 6.43 | 5.62 | 22.1 | 28.5 |
| Benzoic acid | 23.7 | 33.45 | 22.86 | 21.6 | 20.83 | 0.78 | 1.25 | 2.1 | 8.5 | 9.75 |
| By-products (total) | 5.89 | 31.73 | 1.99 | traces | traces | traces | 1.99 | 5.89 | 23.8 | 25.84 |
| TOTAL | 31.45 | 95.56 | 27.53 | 24.55 | 23.67 | 7.76 | 9.67 | 13.61 | 54.4 | 64.10 |

Stream (7) is returned to the oxidation reactor.
Toluene is recovered with conventional means from stream (11)

B. OXIDATION AND PURIFICATION ACCORDING TO THE INVENTION

B.1 Oxidation and purification by distillation (per 100 parts by weight of AB being produced hourly on a continuous basis)

| Streams | (4) | (9) | (11) | (13) | (14) | (15) |
|---|---|---|---|---|---|---|
| Toluene | 377.2 | 1.86 | — | — | — | — |
| Benz-aldehyde | 10.5 | 0.27 | 0.75 | — | — | — |
| Benzoic acid | 130.8 | 12.4 | 7.7 | 100 | 3.6 | 0.34 |
| Benzyl alcohol | 1.6 | 0.3 | 1.3 | — | — | — |
| By-products | 4.7 | 0.68 | 2.45 | 0.8 | 0.14 | 0.68 |
| TOTAL | 524.9 | 15.51 | 12.2 | 100.8 | 3.74 | 1.02 |

B.2 Purification by crystallization

The streams (9), (11), and (14) of 15.51+12.2+3.74=31.45 parts by weight, respectively, are crystallized continuously in accordance with the scheme shown in FIG. 2. From the crystallization system, a yield of 20.83 parts benzoic acid are obtained

We claim:
1. A method of purifying benzoic acid, as obtained by catalytic oxidation of toluene and purification by rectification wherein the secondary streams are cycled back into the oxidation reactor, characterized in that the secondary streams leaving the stripping column are caused to undergo the following sequential steps:
   (a) at least one distillation and at least one crystallization in an organic solvent;
   (b) scrubbing of the crystals from (a) using the same solvent as in (a);
   (c) cycling of the mother liquors from the crystallization as in (a) plus the mother liquors from (b) back into the dissolver;
   (d) further scrubbing of the crystals from (b) using the same solvent as in (a), the scrubbing liquors being cycled back; and optionally
   (d1) further scrubbing of the crystals as scrubbed in (d) with water.
2. A method according to claim 1, characterized in that toluene is used for the solvent in (a), (b) and (d), and the scrubbing liquors are cycled back to the toluene oxidation reactor.

* * * * *